US005589691A

United States Patent [19]

Venkataramani et al.

[11] Patent Number: 5,589,691
[45] Date of Patent: Dec. 31, 1996

[54] PROCESS FOR RECOVERY AND RECYCLE OF METHANESULFONIC ACID AND PHOSPHOROUS ACID

[75] Inventors: Edamanal S. Venkataramani, Woodbridge; Andrew L. Forman, Scotch Plains; Ralph J. Magliette, Jr., Piscataway; William A. Vaughn, Avenel, all of N.J.; Richard R. Dauer, Longmont, Colo.

[73] Assignee: Merck & Co., Inc., Rahway, N.J.

[21] Appl. No.: 254,213

[22] Filed: Jun. 6, 1994

[51] Int. Cl.$^6$ .................................................. C09K 3/00
[52] U.S. Cl. .............................. 252/182.11; 252/182.12
[58] Field of Search ........................... 252/182.11, 182.12

[56] References Cited

U.S. PATENT DOCUMENTS

| | | | |
|---|---|---|---|
| 4,450,047 | 5/1984 | Malzahn | 203/15 |
| 4,922,007 | 5/1990 | Kieczykowski . | |
| 4,938,846 | 7/1990 | Comstock et al. | 203/15 |
| 5,019,651 | 5/1991 | Kieczykowski | 562/13 |
| 5,128,040 | 7/1992 | Mulof et al. . | |

FOREIGN PATENT DOCUMENTS

| | | |
|---|---|---|
| 58-088097 | 8/1983 | Japan . |
| 3-296498 | 12/1991 | Japan . |
| WO9506052 | 3/1995 | WIPO . |

OTHER PUBLICATIONS

M. Afzal and J. Ahmed "Harned/Akerlof Equations and the solubility of NaCl in HCl–water system", Pakistan *J. Sci. Ind. Res.*, vol. 17, No. 6, 1974.

S. C. Baker and J. C. Jurrell, "Microbial Degradation of Methanesulphonic acid: A Missing Link in the Biogeochemical Sulfer Cycle", *Nature*, 350:527–8, 1991.

E. Miller "Vapor–Liquid Equilibria below 0° C of hydrogen chloride solutions saturated with calcium chloride", *J. Chem. Eng. Data*, vol. 35, No. 4:436–440, 1990.

R. W. Potter III, and M. A. Clynne, *J. Chem. Eng. Data*, vol. 25:50–51, 1980.

J. Ruth, "Odor Thresholds and Irritation Levels of Several Chemical Substances: A Review", *Am. Ind. Hyg. Assoc. J.*, 47:141–150, 1986.

T. Sako et al., "Salt effects of vapor–liquid equilibiria for volatile strong electrolyte–water systems", *J. Chem. Eng. Jap* (English), vol. 17, No. 4, 381–388, 1984.

E. S. Venkataramani et al., "Create Drugs, Not Waste—Case Histories of One Company's Successes", *Chemtech*, p. 674, Nov. 1992.

D. E. Wierenga and C. R. Eaton "The Drug Development and Approval Process", p. 10 in *New Drug Approvals in 1992* presented by the Pharm. Mfgs. Assoc., Jan. 1992.

*Primary Examiner*—Donald P. Walsh
*Assistant Examiner*—Anthony R. Chi
*Attorney, Agent, or Firm*—Joanne M. Giesser; Melvin Winokur

[57] ABSTRACT

Disclosed is a process for recovering and recycling waste methanesulfonic acid (MSA) and phosphorous acid ($H_3PO_3$) in a bisphosphonation process for reuse in the process. The recovery process involves treating a waste crude mother liquor stream with HCl to remove sodium ion, as sodium chloride, recovering HCl—$H_2O$ by atmospheric distillation, separating and dehydrating a mixture of methanesulfonic acid and phosphorous acid by vacuum distillation for recycle. The substantially dry methanesulfonic acid and phosphorous acid, and previous HCl, can all be recycled back to the process for reuse.

13 Claims, 5 Drawing Sheets

Overall Chemistry of the Synthetic Process for Alendronate Sodium

Step 1: Bisphosphonation Reaction

γ-Aminobutyric Acid
MW 103.1

Pyrophosphonate
MW 295

+ HCl (g) + Oligomers

Step 2: Aqueous Quench/pH Controlled

Pyrophosphonate
MW 295

Sodium Pyrophosphonate
MW 295

Step 3: Hydrolysis/Crude Crystallization

Sodium Pyrophosphonate
MW 295

Alendronate Sodium
Trihydrate
MW 325.1

Alendronate Sodium

Overall Process Flowsheet with MSA/PO3 Recovery/Recycle

Alendronate Sodium

Phosphorous Removal

PROCESS FOR RECOVERY AND RECYCLE OF METHANESULFONIC ACID AND PHOSPHOROUS ACID

BACKGROUND OF THE INVENTION

1. Field of the Invention

This invention relates to a process for recovering and recycling waste methanesulfonic acid (MSA) and phosphorous acid ($H_3PO_3$) in a bisphosphonation process by separating and dehydrating a mixture of methanesulfonic acid and phosphorous acid by sequential distillation, for reuse in the process.

2. Brief Description of Disclosures in the Art

Alendronate sodium, 4-amino-1-hydroxybutylidene-1-bisphosphonic acid monosodium trihydrate, is a promising new agent for combatting bone resorption in bone diseases including osteoporosis, particularly in post-menopausal women. The compound, utility and method of preparation are described in U.S. Pat. Nos. 4,922,007 and 5,019,651, both assigned to Merck & Co., Inc.

Large scale processes, as described in the above patents, for producing alendronate sodium generate large volumes of materials containing high concentrations of soluble phosphorus-containing materials ($PO_x$) including sodium salts of phosphates, phosphites, pyrophosphates, and methanesulfonic acid/phosphorous acid.

Generally, wastewater treatment processing (WWTP) facilities can handle on a total daily basis about 1–10 ppm (mg/L) phosphorus per liter and 50–500 ppm (mg/L) of MSA.

However, the alendronate process can generate as much as 500 mg of phosphorus and over 1000 mg MSA per liter of waste per day greatly exceeding the allowable limits in many geographic regions for wastewater processing and discharge of effluent.

General methods for dealing with this problem have included industrial incineration, storage and disposal of wastewater materials over extended periods of time at the allowable environmentally imposed limits for $PO_x$ and MSA.

However, incineration suffers from high cost due to the volume of wastes, the low BTU value of the salt solutions and their potential for acidic emissions which could lead to acid rain. Disposal via wastewater treatment, WWT, suffers from the requirements of large corrosion resistant storage tanks used for extended time periods and expensive labor costs due to increased levels of monitoring of WWTP operating parameters.

Other methods include biodegradation of methanesulfonic acid (MSA) using an activated sludge and oxidizing phosphorous acid ($H_3PO_3$) to phosphoric acid ($H_3PO_4$) for easier removal.

However these methods suffer the disadvantage of only being able to process small portions of the waste $PO_x$/MSA for a given biodegradation cycle. Furthermore, efficient biodegradation of MSA can potentially interfere with the ability of the WWTP to degrade other more easily oxidizable substrates. Optimal conditions for the biodegradation of MSA are considerably different from standard WWTP operating conditions, vary from site to site and are disruptive to production scheduling.

What is desired in the art is a process for recovering and recycling methanesulfonic acid, MSA, and phosphorous acid $H_3PO_3$, in an environmentally safe, efficient and cost-effective manner, that has minimal impact on typical WWTP operating parameters.

SUMMARY OF THE INVENTION

Figure 1:
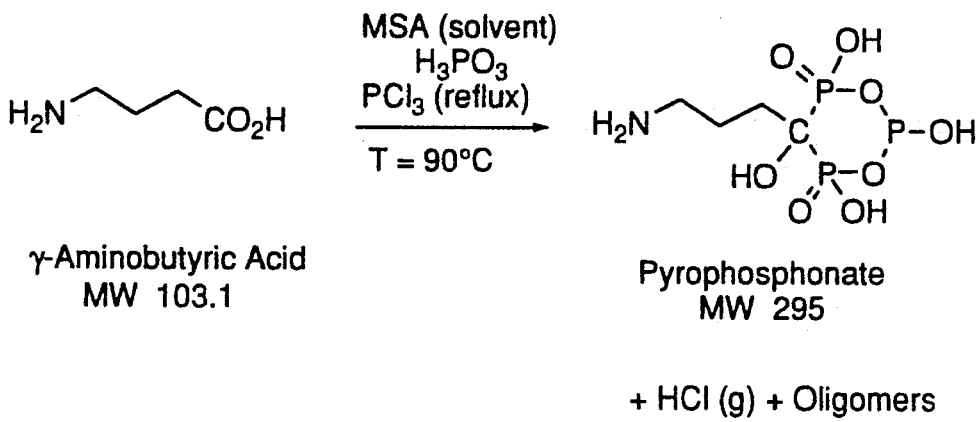
FIG. 1 illustrates the overall chemistry of the bisphosphonate process for producing alendronate sodium.
Figure 1:
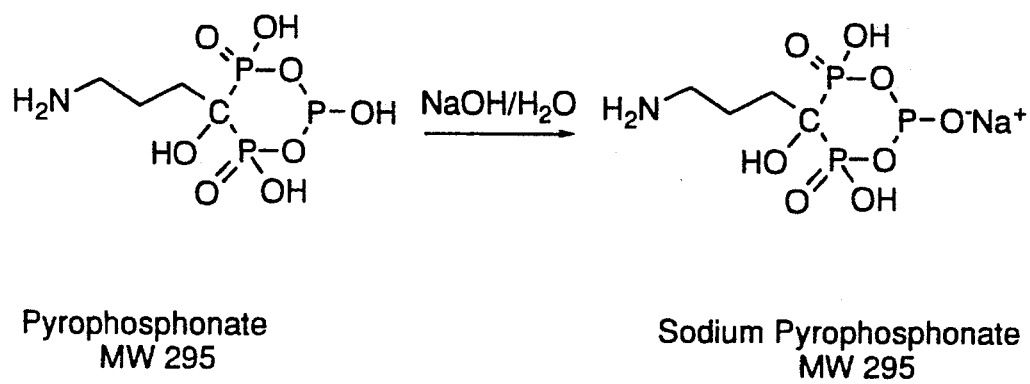
Figure 1:
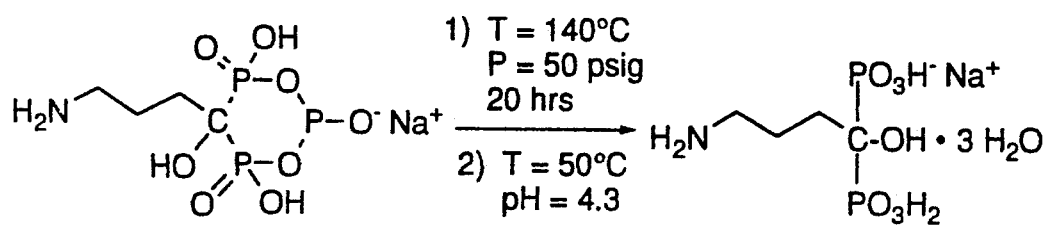

We have found that the waste methanesulfonic acid (MSA) and phosphorous acid ($H_3PO_3$) from the alendronate sodium bisphosphonate process can be efficiently recovered by treating a waste crude mother liquor stream with HCl to remove sodium ion, as sodium chloride, recovering a substantial portion of the HCl—$H_2O$ from the stream by atmospheric distillation, followed by completion of the HCl—$H_2O$ removal from the resultant dry mixture of methanesulfonic acid and phosphorous acid by vacuum distillation. The dry methanesulfonic acid and phosphorous acid mixture can be recycled together back to the process for reuse. The distilled HCl—$H_2O$ can be collected and recycled within the processes.

By this invention there is provided a process comprising the steps of:

(i) contacting an aqueous medium, e.g. solution, of about pH 4–8, containing the sodium salts of methanesulfonic acid and phosphorous acid with hydrochloric acid, being aqueous concentrated HCl or gaseous HCl, to obtain an HCl concentration of about 6N or above to precipitate sodium chloride;

(ii) separating sodium chloride from the aqueous medium, e.g. solution in (i);

(iii) washing the separated sodium chloride with saturated aqueous sodium salt solution, e.g., sodium chloride solution, to remove residual methanesulfonic acid and combining the washing filtrate with the aqueous medium in Step (ii);

(iv) removing hydrochloric acid and water from the resulting combined aqueous media, e.g., filtrates, from Step (ii) and Step (iii) by atmospheric distillation;

(v) separating the small amounts of HCl and $H_2O$ from methanesulfonic acid and phosphorus acid in the resulting medium in Step (iv) by vacuum distillation to yield a dry, solution of methanesulfonic acid/phosphorous acid.

Also there is provided a process comprising the steps of:

a) contacting an aqueous medium of pH 4–8 comprised of the salts e.g., sodium, of omega amino $C_2$–$C_6$ alkylidene-1-hydroxy-1,1-bisphosphonic acid, methanesulfonic acid, phosphorous acid and phosphoric acid, with a calcium chloride compound in an amount of 2–10 parts by weight of calcium chloride, taken as the anhydrous salt, to 100 parts by volume of the medium, at about room temperature;

b) contacting said solution from Step (a) with calcium oxide in a sufficient amount to increase the pH to 11–12 to cause precipitation of calcium/phosphorus containing salts;

c) contacting said mixture from Step (b) with an acid, e.g., hydrochloric acid, to adjust the pH of the aqueous portion of the mixture to about 6–8 to further precipitate said calcium/phosphorus containing salts;

d) separating said precipitated mixture of calcium/phosphorus containing salts from the aqueous medium Step (c);

e) contacting said aqueous medium in Step (d) comprised of the sodium salts of methanesulfonic acid and phosphorus acid with hydrochloric acid to obtain an HCl concentration of about 6N or above to precipitate sodium chloride;

f) separating sodium chloride from the medium in (e);

g) washing the separated NaCl with saturated aqueous sodium salt solution to remove residual methanesulfonic acid;

h) removing a substantial portion of hydrochloric acid and water from the resulting medium in Step (g) by atmospheric distillation;

i) separating methanesulfonic acid and phosphorous acid from the resulting medium in Step (h) by vacuum distillation to yield a substantially dry anhydrous mixture of methanesulfonic acid/phosphorous acid.

BRIEF DESCRIPTION OF THE INVENTION AND PREFERRED EMBODIMENTS

The overall alendronate sodium process chemistry as shown in FIG. 1 includes three steps: a bisphosphonation reaction, a pH controlled aqueous quench, and a hydrolysis/crude crystallization step. The process can be carded out either as a batch or continuous process utilizing standard apparatus.

In the bisphosphonation reaction, (see U.S. Pat. No. 4,922,007) gamma-aminobutyric acid (GABA) is reacted with phosphorus trichloride ($PCl_3$) and phosphorous acid ($H_3PO_3$) in methanesulfonic acid (MSA) as solvent under reflux temperature, e.g. 80°–100° C. for about 0.5 to 3 hours. The reaction can generally be carded out at atmospheric pressure. As seen in FIG. 1, the initial product in the reaction is pyrophosphate (PP) and multimeric alendronate precursors (not shown).

The reaction mixture is then quenched into water under pH control using aqueous caustic at a maintained pH of 4 to 7. Then the pH is adjusted to 4–5, e.g. 4.3–4.7, and then heated under pressure, e.g. 1 to 10 atmospheres, a useful range being 1–4 atmospheres, at a temperature of about 100° to 150° C., a useful range being 135°–145° C., for about 2 to 30 hours, a useful range being 20–24 hours, to substantially convert the pyrophosphate and multimeric precursors to alendronate sodium. The small residual fraction which is not converted alendronate sodium is termed "alendronate by-products".

The crude crystallization is carded out by cooling the hydrolysis mixture to about 0°–60° C., e.g. about 50° C., and adjusting the pH to about 4–5, a useful range being 4.2–4.7, by the addition of aqueous caustic or hydrochloric acid, producing crystalline alendronate sodium (trihydrated) which is filtered, collected, purified and processed.

Figure 2:
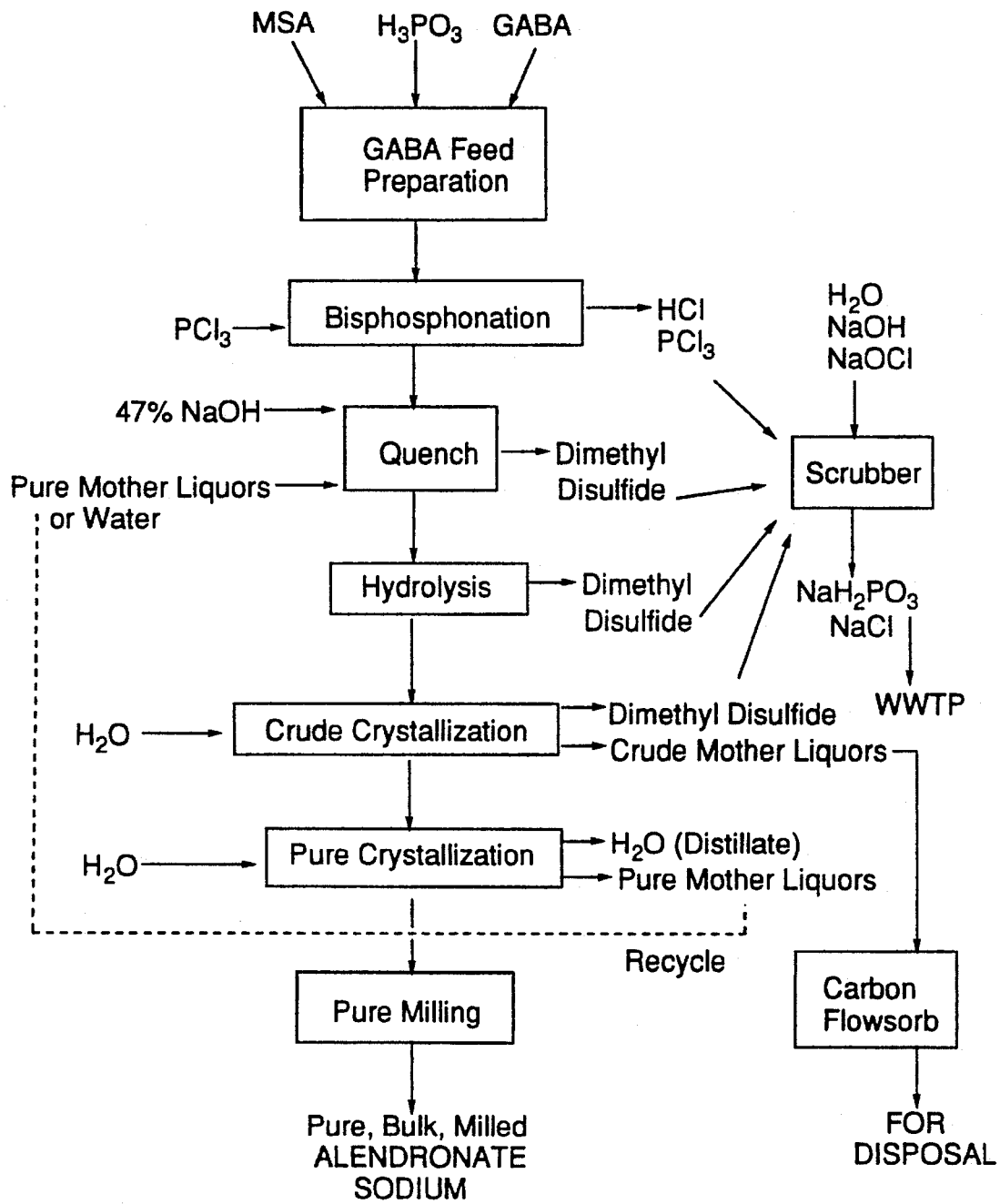
FIG. 2 illustrates the overall bisphosphonate process flowsheet for alendronate sodium manufacture.
Figure 3:
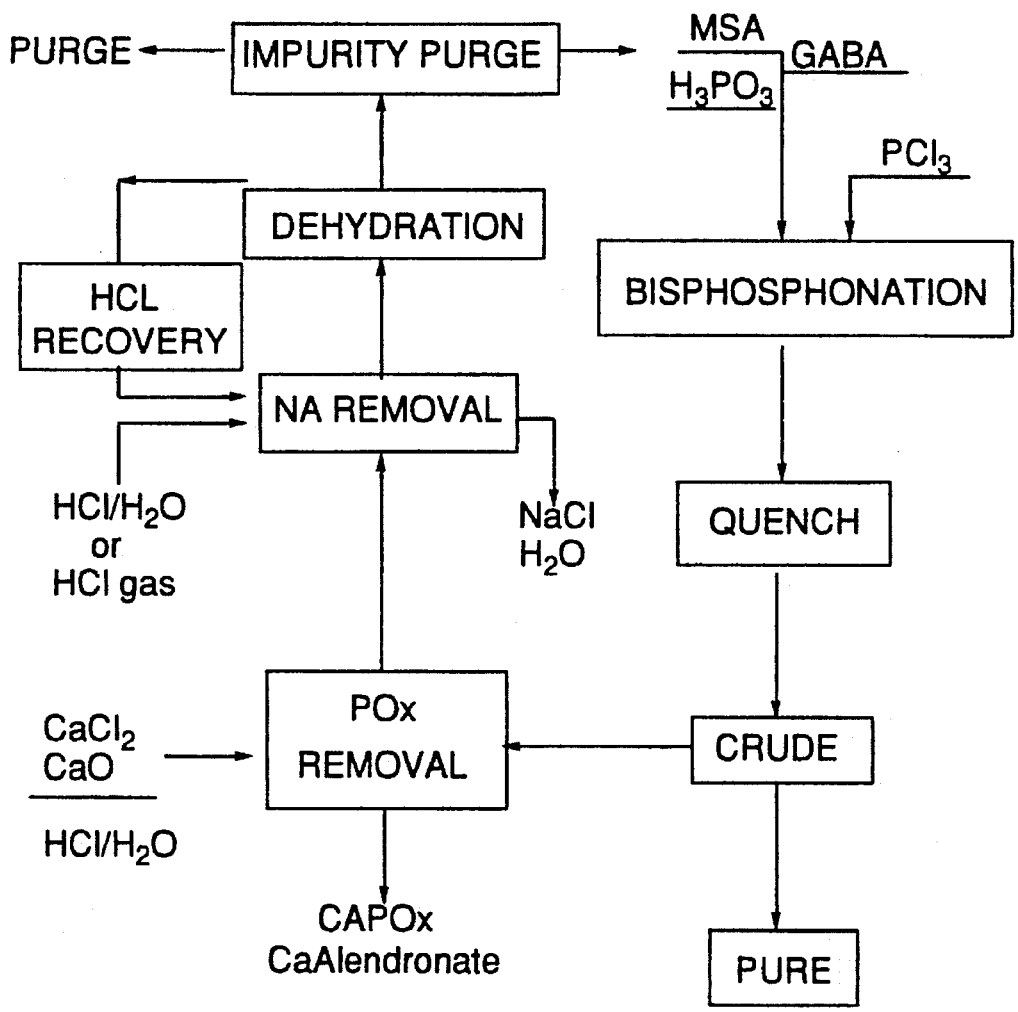
FIG. 3 illustrates the methanesulfonic acid/phosphorous acid recovery step.

The overall process flowsheet for alendronate sodium manufacture is shown in FIG. 2.

As seen, GABA feed is prepared from a mixture of GABA, MSA and $H_3PO_3$ and then fed into the bisphosphonation reaction vessel together with $PCl_3$ to form the pyrophosphate (PP).

After the bisphosphonation step, the reaction mixture is reacted with aqueous caustic in a quench step under controlled pH conditions of pH 4 to 7 to form sodium pyrophosphate (other pyrophosphates not shown) and then heated under elevated pressure and temperature in a subsequent hydrolysis step to form alendronate sodium.

The hydrolysis mixture is cooled, the pH is adjusted to 4 to 5 and alendronate monosodium trihydrate is allowed to precipitate as a crude crystallization mass.

The crude crystallized alendronate sodium is filtered, separated from the crude mother liquors, washed with a minimum volume of cold demineralized (DM) water, and then subjected to a pure crystallization step from demineralized (DM) water.

The pure crystallized alendronate sodium being of pharmaceutically acceptable quality, is collected, and milled to produce pure, bulk, milled alendronate sodium which can be further processed for pharmaceutical dosage formulation.

The gaseous side products from the bisphosphonation reaction, consisting mainly of HCl, $PCl_3$ and the vapors from the vessels used in the quench, hydrolysis and crude steps containing trace amounts of dimethyldisulfide (DMDS), are passed to a scrubber containing water, caustic and sodium hypochlorite to produce a wastewater process stream containing predominantly a mixture of $Na_2HPO_3$, $Na_2HPO_4$, $Na_3PO_3$, $Na_3PO_4$ and sodium chloride which can be disposed of by discharging under controlled conditions. The crude mother liquors (MLs) can be passed over a bed of activated carbon to remove dimethyldisulfide, DMDS, and collected in a tank for MSA/$H_3PO_3$ recovery. Prior to the MSA/$H_3PO_3$ recovery process, $PO_x$ ($PO_4$ as well as $PO_3$ species) and alendronate can be partially or totally removed by the $CaCl_2$/CaO precipitation step described below.

The novel aspect of this invention involves a new way for treatment/recycle/disposal of the waste/excess methanesulfonic acid/phosphorous acid produced and found primarily in the crude mother liquors.

First, excess P (as $PO_4$ and $PO_3$) and residual alendronate sodium are substantially removed from the crude mother liquors using the $CaCl_2$/CaO precipitation step as described in Example 1. Then, sodium, as sodium chloride is removed from the crude mother liquors by adding concentrated HCl or anhydrous HCl, until the mixture is at least 6N HCl or above. Useful ranges are 6N to 10N HCl, and a particularly useful concentration is 8N HCl. The solubility of NaCl in a acidic media in the presence of HCl is low. Since during the alendronate quench step all acid species are neutralized with NaOH during the quench step and pH adjustment prior to the hydrolysis and crude steps, this provides a mechanism whereby sodium can be selectively removed from other anions by adding high concentrations of HCl. At concentrations of HCl above 6N, the solubility of NaCl is <5 g/l, resulting in greater than 90–95% removal of NaCl. This leaves protonated forms of the other anions that are not removed in the calcium precipitation step. At this point, the aqueous filtrate is composed of <5 g/l NaCl plus all of the MSA, a correct proportion of $H_3PO_3$, impurities and a high concentration of HCl. The next steps involve removal of residual HCl and water and the vacuum distillation to yield dry, e.g. substantially anhydrous MSA/$H_3PO_3$, for reuse in the bisphosphonation reaction step. Subsequent HCl recovery and recycle improves the process economics.

HCl removal is accomplished by atmospheric distillation followed by flushing the residue with water. There is a high boiling azeotrope for HCl and water at 108°–110° C. at atmospheric pressure. Generally, about 80 to 90% of HCl and $H_2O$ present can be removed by the atmosphere distillation step leaving 10 to 20% $HCl/H_2O$ present in the residue containing $MSA/H_3PO_3$ to be removed during vacuum distillation. Therefore, in order to achieve complete HCl removal from the $MSA/H_3PO_3$ residue, water flushes must be used, or final HCl removal must be performed during the subsequent vacuum dehydration step.

Finally, $MSA/H_3PO_3$ dehydration is performed by vacuum distillation in a pot or thin film (falling or wiped) evaporator. Typical apparatus for conducting this is described in U.S. Pat. Nos. 4,450,047 and 4,938,846. Due to thermal instability of MSA at its atmospheric boiling point of 265° C., the dehydration step must be performed under vacuum. The boiling point of MSA at 10 mm Hg is 167° C. Generally, the vacuum distillation is conducted in the temperature range of 80° to 110° C., at a reduced pressure of 3–7 mm Hg. A practical set of conditions is a temperature of about 100° C. at 15 mm/Hg. Desirably, the lowest reduced pressure that is practical is utilized to maximize the lowering of the boiling point of MSA. Higher temperatures are avoided to inhibit undesired chemical reactions of MSA. Technology to produce anhydrous MSA from MSA/water mixture is well developed and is currently practiced on a commercial scale (see U.S. Pat. Nos. 4,450,047 and 4,938,846).

If required, an impurity purge can be conducted, consisting of the step of disposing of 0–50%, preferably 20% of the recovered material ($MSA/H_3PO_3$) to avoid excessive buildup of the impurities e.g., of 2-phosphonopyrrolidinone.

The resulting $MSA/H_3PO_3$ mixture contains about 60 to 90 weight percent MSA and 30 to 40 weight percent $H_3PO_3$, generally in about a 4:1 $MSA/H_3PO_3$ weight ratio. The mixture being a homogeneous solution, is "substantially dry" and contains less than 1 weight percent water. Addition of $PCl_3$ in an amount to just react with the residual water present, results in anhydrous $MSA/H_3PO_3$ mixtures for recycle.

The economics of the MSA recovery process are linked directly to the need for HCl to both protonate the entire sodium load and saturate the process stream up to a minimum of 6N. After removal of sodium as NaCl, all of the HCl must be removed and, if disposed, must be neutralized by addition of NaOH. Thus, on a once through basis, a huge inventory of HCl and NaOH would be required to achieve the sodium removal step. In consideration of this cost, a recovery step for dilute HCl was developed. The process takes note of the usual industrial practice for concentrating dilute HCl. First, $H_2O$ is distilled off typically in a multi-plate column to achieve the high boiling atmosphereic azeotrope. Then, $CaCl_2$ is added to the concentrated HCl in order to break the high boiling azeotrope between HCl and water during a subsequent atmospheric distillation. The azeotrope is completely eliminated by the addition of >75 mM $CaCl_2$. Implementation of this process requires a single stage distillation for the initial stage that includes a high concentration of $CaCl_2$. Very high vapor pressures of HCl are achieved. The level of partial reflux is then adjusted to achieve ~50 wt % HCl in the distillate which can then be recycled for use in the sodium chloride precipitation step where very strong HCl is needed to achieve a concentration of 6N HCl or higher.

Figure 4:
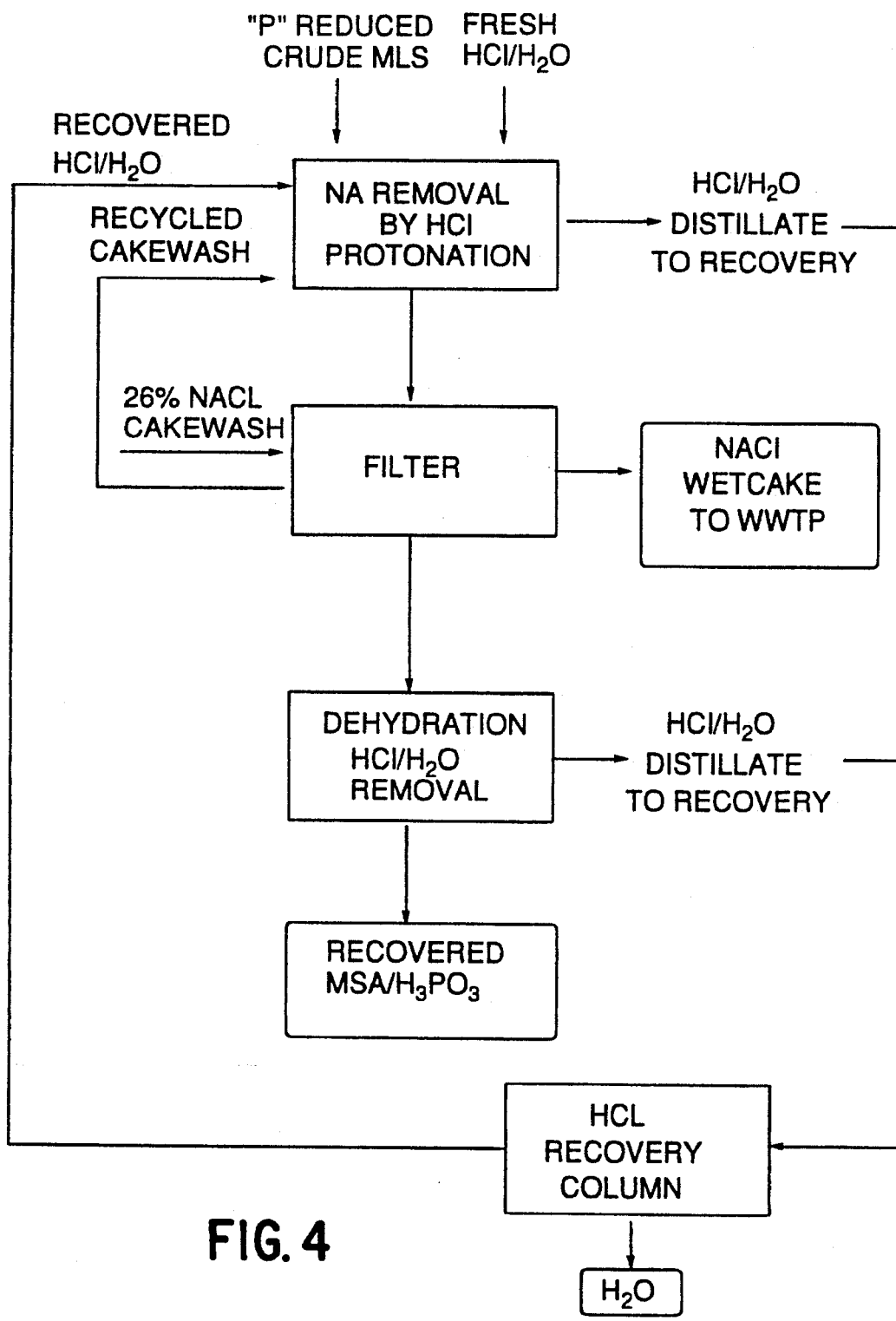
FIG. 4 illustrates the overall solvent recovery process including the methanesulfonic acid/phosphorous acid recovery step.

A flowsheet incorporating the key process elements: (1) Na removal by HCl saturation, (2) HCl recovery by pot distillation, (3) $MSA$/phosphorous acid dehydration by falling film evaporation, and (4) dilute HCl recovery/concentration by $CaCl_2$ column distillation is given in FIG. 4. The process can be run on a continuous basis to minimize surge volumes for the various steps. This process can be nm in parallel with the bisphosphonation reaction step and provide essentially quantitative recovery of MSA and >25% muse of the total P as $PO_3$. Recovered MSA and $H_3PO_3$ from this process has been successfully used in the bisphosphonation reaction. The results show that the recovered MSA and $H_3PO_3$ can be reused without any yield or quality penalty.

Figure 5:
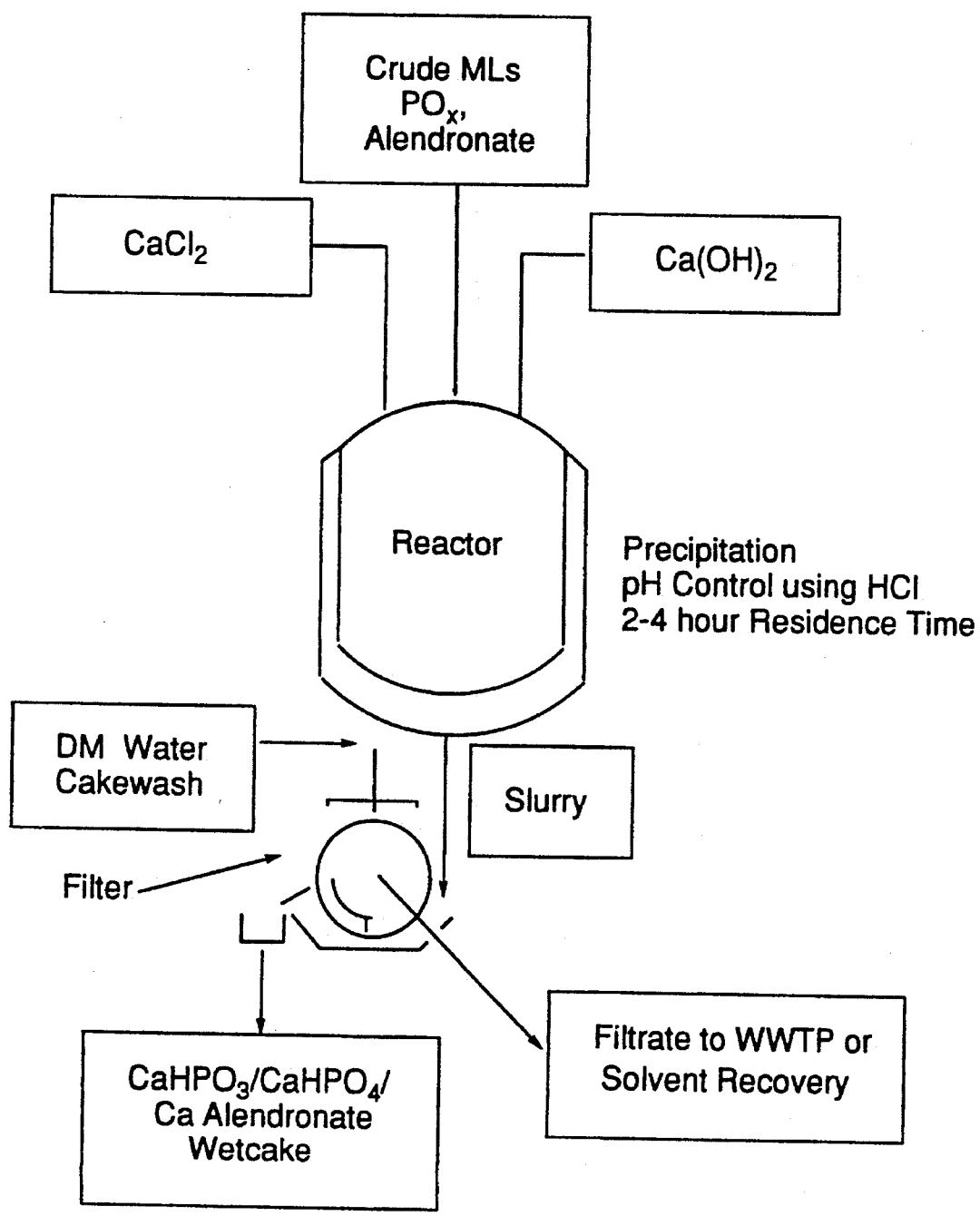
FIG. 5 illustrates the calcium precipitation/phosphorous removal step.

In the calcium precipitation step, prior to $MSA/H_3PO_3$ recover, the crude mother liquors are passed to a precipitation tank for $CaCl_2$/lime/pH adjustment as shown in FIG. 5.

The crude mother liquors (MLs) initially contain about 5–10% by weight phosphate and phosphite as $PO_X$, 22–25% MSA, 5% NaCl, 1–2% GABA, 0–0.05% alendronate sodium and byproducts and 60–65% water.

The processed mother liquors, after partial $PO_X$ removal by CaO precipitation, but just prior to the $MSA/H_3PO_3$ recovery process of the instant invention, contains about 0–3% by weight phosphate and phosphite as $PO_X$, 12–25% MSA, 4–6% NaCl, 1–2% GABA, 0–0.05% alendronate sodium and byproducts, and 60–80% water.

In the initial step, $CaCl_2$ is added in an amount of about 2 to 10 weight percent by volume of mother liquor, and usually 2–4 w/v percent taken as anhydrous $CaCl_2$. The $CaCl_2$ is generally used for convenience, as the hexahydrate although the anhydrous form, being expensive, can also be used. The purpose of adding $CaCl_2$ first in the process is to increase the ionic strength of the liquid medium and to salt out subsequently formed calcium/phosphorus salts.

Next. CaO (lime) is added in sufficient quantity., usually 3–7, weight by volume percent, and usually about 5 w/v percent, to produce a pH of about 10–12 to facilitate subsequent precipitation of the $PO_X$ species.

Next, the mixture is neutralized by the addition of e.g. hydrochloric acid to lower the pH to about 6–8, e.g., 7. The resulting slurry is stirred for about 2–4 hours to insure maximum possible precipitation of all the $PO_X$ species in the mother liquors.

Eliminating the $CaCl_2$ addition or the neutralization step, all result in lowered $PO_X$ recovery. $PO_X$ recovery of about 90– 95+% are achieved by this disclosed invention method. However, using the CaO step alone gives about 60% recovery. Furthermore, using the $CaCl_2$/CaO addition without the neutralization step results in about 88% recovery.

An additional advantage of this $PO_X$ removal methodology is that residual alendronate sodium, being the active drug ingredient, as well as alendronate byproducts are also selectively and quantitatively removed from the $PO_X$ filtercake, satisfying environmental concerns.

After the CaO precipitation, the slurry is filtered and washed with water, a useful form being demineralized (DM) water. The filtrates are cycled to the wastewater treatment plant (WWTP), or to solvent recovery, or if sufficiently low in $PO_X$, to a separate bacterial biodegradation step for MSA treatment prior to passing to WWTP.

A microbial biodegradation step can be used involving an acclimated sludge culture for biodegrading MSA, in which increasing concentrations of MSA in wastewater are fed to the sludge while maintaining the pH, BOD, hydraulic residence time and sludge density within optimized process limits.

The precipitated $PO_X$ filtercake, which contains predominantly $CaHPO_3$, $CaHPO_4$ and calcium alendronate, is dried and used on landfill, incinerated or recycled to a fertilizer plant for extraction of usable phosphorus.

At moderate production levels, this process can be carded out in batch mode. However, the $PO_x$ reduction process is also very amenable to continuous operation at full production scale.

The $PO_x$ removal efficiencies in the process are a function of the reagents used and the pH. An alternative reagent useful in the precipitation of $PO_x$ is $Al(OH)_3$, but this only adds a new cation to an already complex waste stream. Also, $Al^{+++}$ was found to be less effective than $Ca^{++}$ in the removal of $PO_x$ from this stream.

The described $PO_x$ recovery process can also be used in other bisphosphonation processes where the appropriate amino acid starting material can be used to produce the following omega amino $C_2$-$C_6$ alkylidene-1,1-bisphosphonic acids: 2-amino-1-hydroxyisobutylidene-1,1-bisphosphonic acid, 3-amino-1-hydroxy-propylidene-1,1-bisphosphonic acid, 5-amino-1-hydroxypentylidene-1,1-bisphosphonic acid and 6-amino-1-hydroxyhexylidene-1,1-bisphosphonic acid. The term "omega amino" is used herein to indicate the presence of an amino group on the terminal carbon of the alkylidene chain at the other end from the bisphosphonate carbon atom.

The following examples are illustration of carrying out the invention as contemplated by the inventors.

EXAMPLE 1

$CaCl_2$/CaO/Neutralization

To 1 liter of alendronate sodium Crude MLs (pH~4.5) at room temperature (20°–25° C.), is added 70 g of calcium chloride ($CaCl_2$) and stirred for 15 minutes (pH~4, T=20°–25° C.).

Next, 50 g of lime (CaO), is added and mixed rapidly for 30 minutes (pH 12). The pH and temperature generally increase to about 12° and ~45° C., respectively.

Next, concentrated HCl (36%) is added to adjust the pH of the mixture to about 7. Several additions of HCl may be required to stabilize the pH to 7. Approximately 75 mL of 36% HCl is required. Neutralization is complete when the pH is stabilized at about 7, for at least 10 minutes. The temperature rise is usually minimal ($\leq 5°$ C.).

The mixture is allowed to stir for 5 minutes, then filtered using a Whatman #4 filter paper in a Buchner Funnel using vacuum. The filtercake is washed with 2–5 volumes of DM water to remove residual MSA from the $CaHPO_x$ filtercake. The washings are combined with the filtrate for MSA recover. The total time for filtration is generally about $\leq 1$ hr.

The filtrate can be treated by an activated sludge system described above. The cake is saved for ultimate disposal.

The $PO_x$ removal efficiency is 96–98%.

The overall process for the removal of $PO_x$ can be written as:

Crude MLs+70 g/L $CaCl_2$ (mixing) +50 g/L lime (mixing) +pH adjustment using HCl to ~7, followed by filtration and DM water wash.

Repeating the above process in the absence of the $CaCl_2$ addition and neutralization steps results in a $PO_x$ recovery of only about 60%

Repeating the above process in the absence of the final pH neutralization step only results in a $PO_x$ recovery of about 88%.

References

Afzal, M. and Ahmed, J., "Harned/Akerlof Equations and the solubility of NaCl in HCl-water system", Pakistan J., Sci. Ind. Res., Vol. 17, No. 6, 1974.

Baker, S. C., Kelly, D. P., and Murrell, J. C., "Microbial Degradation of Methanesulphonic acid: A Missing Link in the Biogeochemical Sulfur Cycle", Nature, 350:527–8, 1991.

Linke, W. F. "Solubilities of Inorganic and Metal Organic Compounds", 4th ed., Vol. 2, American Chemical Society, Washington, D.C., 1965.

Miller, E., "Vapor-Liquid Equilibria below 0° C. of hydrogen chloride solutions saturated with calcium chloride", J. Chem. Eng. Data (1990), Vol. 35, No. 4, 436–440.

Potter, R. W. II and Clynne, M. A., J. Chem Eng. Data (1980) Vol. 25, 50–51.

Ruth, J., "Odor Thresholds and Irritation Levels of Several Chemical Substances: A Review", Am. Ind. Hyg. Assoc. J., 47, 142–150, 1986.

Sako, T., Jakuta, T., Yoshitoma, H., "Salt effects of vapor-liquid equilibria for volatile strong electrolyte-water systems", J. Chem. Eng. Japan (English), Vol. 17, No. 4, 381–388, 1984.

U.S. Pat. No. 4,938,846 to Comstock, et al. assigned to ATOCHEM North America, Inc.).

U.S. Pat. No. 4,922,007 to Kieczykowski, et al. (assigned to Merck & Co., Inc.).

U.S. Pat. No. 4,450,047 (assigned to Elf-Atochem).

U.S. Pat. No. 5,019,651 (assigned to Merck & Co., Inc.).

Venkataramani, E. S., Vaidya, F., Olsen, W. and Wittmer, S., "Create Drags, Not Waste—Case Histories of One Company's Successes", Chemtech, p. 674, November 1992.

Wierenga, D. E. and Eaton, C. R., "The Drug Development and Approval Process", page 10 in "New Drug Approvals in 1992" presented by the Pharmaceutical Manufacturers Association, January 1992.

What is claimed is:

1. A process comprising the steps of:
   (i) contacting an aqueous medium comprised of the sodium salts of methanesulfonic acid and phosphorous acid with hydrochloric acid to obtain an HCl concentration of about 6N or above to precipitate sodium chloride;
   (ii) separating sodium chloride from the aqueous medium in (i);
   (iii) washing the separated sodium chloride with saturated aqueous sodium salt solution to remove residual methanesulfonic acid;
   (iv) removing hydrochloric acid and water from the resulting medium in Step (iii) by atmospheric distillation;
   (v) separating methanesulfonic acid and phosphorous acid from the resulting medium in Step (iv), which contains small amounts of HCl and $H_2O$, by vacuum distillation to yield a dry mixture of methanesulfonic acid/phosphorous acid.

2. The process of claim 1 wherein said HCl concentration is in the range of 6N to 10N HCl.

3. The process of claim 2 wherein said HCl concentration is 8N HCl.

4. The process of claim 1 wherein Step (iv) is conducted at temperature in the range of about 108°–110° C. at atmospheric pressure.

5. The process of claim 1 wherein Step (iv), about 80 to 90 percent of HCl and $H_2O$ are removed.

6. The process of claim 1 wherein Step (v) said vacuum distillation is conducted at a temperature of 80° to 110° C. under a reduced pressure of 3 to 7 mm Hg.

7. The process of claim 5 wherein said temperature is about 100° C. and said reduced pressure is about 5 mm Hg.

8. The process of claim 1 wherein Step (v) the resulting mixture is about 60 to 90 weight percent MSA and 30 to 10 weight percent phosphorous acid.

9. The process of claim 1 wherein said alkaline aqueous solution of Step (i) further comprises an omega amino $C_2$–$C_6$ alkylidene-1,1-bisphosphonic acid is selected from 4-amino-1-hydroxybutylidene-1,1-bisphosphonic acid, 2-amino-1-hydroxyisobutylidene-1,1-bisphosphonic acid, 3-amino-1-hydroxypropylidene-1,1-bis-phosphonic acid, 5-amino-1-hydroxypentylidene-1,1-bisphosphonic acid and 6-amino-1-hydroxyhexylidene-1,1-bisphosphonic acid.

10. The process of claim 9 wherein said omega amino $C_2$–$C_6$ alkylidene-1,1-bisphosphonic acid is 4-amino-1-hydroxybutylidene-1,1-bisphosphonic acid.

11. A process comprising the steps of:
 a) contacting an aqueous medium comprised of salts of omega amino $C_2$–$C_6$ alkylidene-1-hydroxy-1,1-bisphosphonic acid, methanesulfonic acid, phosphorous acid and phosphoric acid, with a calcium chloride compound in an amount of 2–10 parts by weight of calcium chloride, taken as the anhydrous salt, to 100 parts by volume of the medium;
 b) contacting said solution from Step (a) with calcium oxide in a sufficient amount to to cause precipitation of calcium/phosphorus containing salts;
 c) contacting said mixture from Step (b) with acid to adjust the pH of the aqueous portion of the mixture to about 6–8 to cause substantially complete precipitation of said calcium, phosphorous containing salts;
 d) separating said precipitated mixture of calcium/phosphorus containing salts from the aqueous medium;
 e) contacting said aqueous medium in Step (d) comprised of salts of methanesulfonic acid and phosphorus acid with hydrochloric acid to obtain an HCl concentration of about 6N or above to precipitate sodium chloride;
 f) separating sodium chloride from the medium in (e);
 g) washing the separated sodium chloride with saturated aqueous sodium salt solution to remove residual methanesulfonic acid;
 h) removing hydrochloric acid and water from the resulting medium in Step (g) by atmospheric distillation;
 i) separating methanesulfonic acid and phosphorous acid from the resulting medium in Step (h) by vacuum distillation to yield a substantially dry anhydrous mixture of methanesulfonic acid/phosphorous acid.

12. The process of claim 11 wherein said omega amino $C_2$–$C_6$ alkylidene-1,1-bisphosphonic acid is selected from 4-amino-1-hydroxybutylidene-1,1-bisphosphonic acid, 2-amino-1-hydroxyisobutylidene-1,1-bisphosphonic acid, 3-amino-1-hydroxypropylidene-1,1-bisphosphonic acid, 5-amino-1-hydroxypentylidene-1,1-bisphosphonic acid and 6-amino-1-hydroxyhexylidene-1,1-bisphosphonic acid.

13. The process of claim 12 wherein said omega amino $C_2$–$C_6$ alkylidene-1,1-bisphosphonic acid is 4-amino-1-hydroxybutylidene-1,1-bisphosphonic acid.

\* \* \* \* \*